United States Patent
Roy et al.

(10) Patent No.: US 8,425,502 B2
(45) Date of Patent: Apr. 23, 2013

(54) PROBE, SLEEVE, SYSTEM, METHOD AND KIT FOR PERFORMING PERCUTANEOUS THERMOTHERAPY

(75) Inventors: Jean-François Roy, Québec (CA); Patrice Montminy, Charny (CA)

(73) Assignee: Centre Hospitalier Universitaire de Québec, Québec, QC (CA)

( * ) Notice: Subject to any disclaimer, the term of this patent is extended or adjusted under 35 U.S.C. 154(b) by 1020 days.

(21) Appl. No.: 12/375,493

(22) PCT Filed: Jul. 30, 2007

(86) PCT No.: PCT/CA2007/001347
§ 371 (c)(1),
(2), (4) Date: May 8, 2009

(87) PCT Pub. No.: WO2008/011730
PCT Pub. Date: Jan. 31, 2008

(65) Prior Publication Data
US 2009/0264876 A1    Oct. 22, 2009

Related U.S. Application Data

(60) Provisional application No. 60/820,612, filed on Jul. 28, 2006.

(51) Int. Cl.
*A61B 18/18* (2006.01)

(52) U.S. Cl.
USPC .......................................................... 606/21

(58) Field of Classification Search ............... 604/20–23
See application file for complete search history.

(56) References Cited

U.S. PATENT DOCUMENTS 3,800,552 A    4/1974 Sollami et al.
4,211,231 A    7/1980 Rzasa (Continued)

FOREIGN PATENT DOCUMENTS
WO    WO00/71037    11/2000

OTHER PUBLICATIONS

Healthcare Sales & Marketing Network NewsFeed, "Endocare Announces Plan to Deploy Next Generation Cryoablation Technology for New Applications", News Release of Nov. 17, 2005, Internet page: http://salesandmarketingnetwork.com/news_release.php?IP=2008546.

(Continued)

*Primary Examiner* — Victoria P Shumate
*Assistant Examiner* — Diva K Chander
(74) *Attorney, Agent, or Firm* — Benoît & Côté

(57) ABSTRACT

A cryosurgical probe that is operative to bring target nerve tissue to a temperature below about −140° C. so as to reduce or eliminate regeneration of the nerve tissue by growing an ice ball. The probe comprises a thermally conductive body, a thermally insulating body and a temperature sensor. The thermally conductive body has a conductive portion adapted to contact the tissue and form an ice ball thereat during use. The thermally insulating body is adjacent to the conductive portion onto which the ice ball forms during use. The temperature sensor is positioned at a predetermined position on the thermally insulating body with respect to the conductive portion. The predetermined position corresponds to a predetermined size of the ice ball grown in the tissue when the sensor reads a predetermined temperature. The insulating body provides sufficient thermal insulation between the conductive body and the surrounding tissue so that the sensor detects freezing of. The surrounding tissue is in contact with the sensor by growth of the ice ball from the conductive portion onto the insulating body. A sleeve for fitting to a probe and a kit comprising at least two sleeves or two probes, each having one sensor but positioned at different locations is also disclosed. Furthermore, a system using a controller for shutting down a cooling of the probe and methods for performing percutaneous thermotherapy by fitting a sleeve on a probe or by shutting down the cooling of the probe are also disclosed.

39 Claims, 10 Drawing Sheets

U.S. PATENT DOCUMENTS

| | | | |
|---|---|---|---|
| 5,702,435 A | 12/1997 | Maytal | |
| 5,906,612 A * | 5/1999 | Chinn | 606/20 |
| 6,190,378 B1 * | 2/2001 | Jarvinen | 606/21 |
| 6,270,493 B1 | 8/2001 | Lalonde et al. | |
| 6,280,439 B1 | 8/2001 | Martin et al. | |
| 6,551,309 B1 * | 4/2003 | LePivert | 606/20 |
| 6,643,535 B2 | 11/2003 | Damasco et al. | |
| 6,709,431 B2 | 3/2004 | Lafontaine | |
| 6,858,025 B2 * | 2/2005 | Maurice | 606/21 |
| 7,083,612 B2 * | 8/2006 | Littrup et al. | 606/21 |
| 2003/0055415 A1 | 3/2003 | Yu et al. | |
| 2004/0024391 A1 * | 2/2004 | Cytron et al. | 606/21 |

OTHER PUBLICATIONS

Israel21c, "Galil Medical Freezes Cancer Tumors into Oblivion", Mar. 25, 2002, Internet page: http://www.israel21c.org/bin/en.jsp?enScript=PrintVersion.jsp&enDispWho=Articles^1108.

International Search Report of International Patent Application No. PCT/CA2007/001347.

* cited by examiner

PROBE, SLEEVE, SYSTEM, METHOD AND KIT FOR PERFORMING PERCUTANEOUS THERMOTHERAPY

FIELD OF THE INVENTION

The present invention relates generally to the field of systems for percutaneous thermotherapy. More particularly, the invention relates to an improved cryoprobe used in cryosurgery.

BACKGROUND OF THE INVENTION

The treatment of back pains still remains a challenge for many reasons. One of such reasons is the difficulty to permanently and exclusively cure the cause of such pains without affecting surrounding tissues in an area of a human body that is a main channel of nerve impulse.

Different causes of back pain exist. Of all chronic low back pain problems, about 20% can be attributed to the facet joints. This cause is also known as the chronic lumbar facet joint syndrome. Among patients, 90% are successfully treated through conservative procedures such as active physiotherapy and NSAIDS. For the remaining 10%, further investigation as well as a more aggressive therapeutic approach must be considered. Once the diagnosis of the facet joint syndrome is clinically made, percutaneous thermotherapy procedures may be considered, seeking a minimally invasive treatment with low morbidity and satisfactory clinical efficiency.

Discogenic back pain, another cause of back pain, is responsible for close to 60% of chronic low back pain in the general population. Once conservative treatment has been fully used, 5% of the patients remain with back pain that can be considerably invalidating. Usual treatment of this invalidating condition is spinal fusion or disc arthroplasty, both associated with considerable morbidity, off-work time, and social cost. Clinically discogenic pain patients have constant back pain that is amplified in the vertical disc loading positions, with a sitting being even worse or equal to the standing position pain. Disc pain is reproduced by pain provocation procedures such as discograms or discometry. Denervation of a portion of the disc, to relieve some if not most of the pain by a percutaneous procedure, is a known advantageous alternative with a reduction of the cited disadvantages of the more aggressive procedures.

Cryotherapy exists as therapy of discogenic back pain or facet joint syndrome since 1961. However, this technique originally used liquid nitrogen as coolant, reaching a treatment temperature of approximately −80 C.°., while the trocar was placed under fluoroscopic guidance. Limited control of the cryoanalgesia process with this combination of technology has resulted in only temporarily pain relief. Studies even showed that there does not exist statistical differences between patients who had such a treatment and patients treated with a placebo pr probe. On the other hand, a study showed that irreversible damage to the nervous structures is obtained only when temperatures reach below −140 C.°. Temperatures above −140 C.° only temporarily affect the nerve tissue.

It is therefore possible to divide thermotherapy in two types: moderate and extreme temperature thermotherapy. Moderate temperature thermotherapy only temporarily affects nerve tissues and therefore does not cause permanent damages. Consequently, pain relief is only temporary. Monitoring of such treatments is not as critical as it is with extreme temperature thermotherapy. Should the probe affect tissues that should not have been affected, the effects would only be temporary. Extreme temperature thermotherapy (either extremely high or extremely low temperatures), on the other hand, causes permanent damages to tissues. Destroying tissue with this type of treatment is desirable in order to permanently remove pain generators in a body by destroying the nerves in tissues of any nature, or to treat tumors of any kind in a minimally invasive fashion, such as percutaneously. Because of its permanent effects on the body, careful monitoring of the effects of a probe used for extreme temperature treatment is mandatory. Furthermore, cold, whose propagation is far more predictable in the human body than heat, is more often used for extreme temperature treatment. It follows that careful monitoring of a growth of an ice ball of treated tissues created by a cryoprobe is necessary, especially when treating chronic lumbar facet joint syndrome, where inadequate propagation of the ice ball could affect spinal tissues and permanently paralyze a patient. Up to now, monitoring the size of the ice ball was realized either by imagery or by temperature monitoring. Temperature monitoring is accomplished by positioning a temperature sensor that will detect a variation in a temperature of the surrounding tissues and, consequently, the presence of the ice ball. Doing so requires separately inserting in the patient's body the cryoprobe and at least one temperature sensor. Then, X-ray, or another imaging method, must be used to verify a position of the temperature sensor with respect to the cryoprobe.

Imagery monitoring typically uses technologies such as MRI, CT scanning, or ultrasound. However, simultaneously using such imagery systems while operating adds to the complexity of the operation.

Different types of cryoprobes have been suggested. For example, U.S. Pat. No. 6,551,309 describes a cryoprobe comprising, at its tip, several sensors used to monitor that the tip is cooled. However, these sensors are laid out on a thermally and electrically conductive surface and are therefore only adapted to measure the temperature of the tip of the cryoprobe but not that of the surrounding tissues. Consequently, this cryosurgery system requires the use of an MRI imaging system.

US patent application No. 20040024391 describes an apparatus and a method to protect certain tissues during a cryosurgery. This document describes a probe provided with a temperature sensor laid out on a portion remote from its tip. The temperature sensor is used to follow a change of the induced temperature to treated tissues. However, this document does not disclose placing the temperature sensor at a specific distance from the tip such as to monitor the growth of an ice ball and control the cooling by the probe accordingly. Consequently, the apparatus and method described in this document still requires the use of an imagery method such as X rays, ultrasounds, CT or MRI.

There is therefore a need for an improved system for percutaneous thermotherapy that does not require constant visual monitoring of the surgery so that such treatment may be conducted without resorting to imagery systems, which may not be available in all health facilities, and that does not require the use of an additional external temperature sensor.

SUMMARY OF THE INVENTION

It is therefore an object of the present invention to provide a system for percutaneous thermotherapy that overcomes the above drawbacks.

It is another object of the present invention to provide a system for percutaneous thermotherapy that does not necessarily require special imagery systems.

It is another object of the present invention to provide a system for percutaneous thermotherapy that automatically stops the cooling of a conductive portion of the probe when an ice ball of treated tissues has reached a predetermined size.

It is another object of an aspect of the present invention to provide an insulated portion having one or more sensors that is capable of being accurately positioned on an existing probe for thermotherapy.

According to one aspect of the invention, there is provided a cryosurgical probe that is operative to bring target nerve tissue to a temperature below about −140° C. so as to reduce or eliminate regeneration of the nerve tissue by growing an ice ball. The probe comprises a thermally conductive body, a thermally insulating body and a temperature sensor. The thermally conductive body has a conductive portion adapted to contact the tissue and form an ice ball thereat during use. The thermally insulating body is adjacent to the conductive portion onto which the ice ball forms during use. The temperature sensor is positioned at a predetermined position on the thermally insulating body with respect to the conductive portion. The predetermined position corresponds to a predetermined size of the ice ball grown in the tissue when the sensor reads a predetermined temperature. The insulating body provides sufficient thermal insulation between the conductive body and the surrounding tissue so that the sensor detects freezing of the surrounding tissue in contact with the sensor by growth of the ice ball from the conductive portion onto the insulating body.

In a variation of this aspect of the invention, the conductive body is located at a distal tip of the probe opposed to a grabbing end. Such a probe may be used for treating lumbar discs pain.

In another variation of this aspect of the invention, the insulating body is located at the distal tip of the probe opposed to the grabbing end. Such a probe may be used for treating spinal facet joint syndrome.

In another aspect of the invention, there is provided a method of manufacturing a cryosurgical probe as defined here above. The method comprises the step of determining the predetermined position as a function of a desired ice ball size and thermal characteristics of the surrounding tissue.

In yet another aspect of the invention, there is provided a sleeve for fitting to a cryosurgical probe having a conductive portion. The sleeve is operative to bring target nerve tissue to a temperature below about −140° C. so as to reduce or eliminate regeneration of the nerve tissue by growing an ice ball. The sleeve comprises a thermally insulating body and a temperature sensor. The temperature sensor is positioned on the thermally insulating body so that when the sleeve is installed on the cryosurgical probe, the temperature sensor is at a predetermined position with respect to the conductive portion of the cryosurgical probe. The predetermined position corresponds to a predetermined size of the ice ball grown in the tissue when the sensor reads a predetermined temperature. The insulating body provides sufficient thermal insulation between the conductive body and surrounding tissue that the sensor detects freezing of the surrounding tissue being in contact with the sensor by growth of the ice ball from the conductive portion onto the insulating body.

In a variation of this aspect of the invention, the sleeve has a closed ended tip and the conducting body is located at the tip. This type of sleeve may be used for treating lumbar discs pain.

In another variation of this aspect of the invention, the sleeve has a closed ended tip and the insulating body is located at the tip. This type of sleeve may be used for treating spinal facet joint syndrome.

In yet another aspect of the invention, there is provided a method of manufacturing a sleeve as defined here above. The method comprises the step of determining the predetermined position as a function of a desired ice ball size and thermal characteristics of the surrounding tissue.

In a further aspect of the invention, there is provided a system for percutaneous thermotherapy for use with a cryosurgical probe having a conductive portion. The system comprises a controller and a sleeve as defined here above. The sleeve is adapted to be placed on the probe so that the sensor is at a predetermined longitudinal position from the conductive portion. The sensor is operative to send a signal to the controller. The controller is operative to control a cooling of the conductive portion based on the signal sent by the sensor.

In another aspect of the invention, there is provided a method of manufacturing such a system for percutaneous thermotherapy. The method comprises the step of determining the predetermined position as a function of a desired ice ball size and thermal characteristics of the surrounding tissue.

In yet a further aspect of the invention, there is provided a system for percutaneous thermotherapy comprising a controller and a probe as defined here above. The sensor of the probe is operative to send a signal to the controller. The controller is operative to control a cooling of the conductive portion based on the signal sent by the sensor.

In another aspect of the invention, there is provided a method of manufacturing such a system for percutaneous thermotherapy. The method comprises the step of determining the predetermined position as a function of a desired ice ball size and thermal characteristics of the surrounding tissue.

In yet another aspect of the invention, there is provided a method for performing percutaneous cryotherapy using a cryosurgical probe. The method comprises the step of selecting an insulating body having a temperature sensor adapted to be placed at a predetermined distance from a conductive portion of the probe, based on a desired size of an ice ball of tissues surrounding the conductive portion.

In yet another aspect of the invention, there is provided a method for performing percutaneous cryotherapy that comprises the step of automatically shutting down by a controller an imposed thermal variation of a conductive portion of a cryoprobe inserted in a patient's body once a signal from a single temperature sensor placed on a thermally insulating portion of the cryoprobe for sensing a size of an ice ball in surrounding tissues has reached a threshold value.

In still another aspect of the invention, there is provided a kit comprising at least two cryosurgical probes as defined here above. Each one of the probes has its temperature sensor located at a different longitudinally distance from the conductive portion.

In yet another aspect of the invention, there is provided a kit comprising at least two sleeves as defined here above. Each one of the sleeves has its temperature sensor located at a different longitudinally position.

BRIEF DESCRIPTION OF THE DRAWINGS

These and other features of the invention will become more readily apparent from the following description in which reference is made to the appended drawings wherein.

DETAILED DESCRIPTION OF THE INVENTION

The present invention may be used for thermotherapy, either by submitting a patient to heat or to cold. Because transmission of cold in a human body is more predictable than transmission of heat, cryotherapy is more often used. Hence, the present invention will now be described with respect to a cryoprobe used for cryosurgery.

Figure 1:
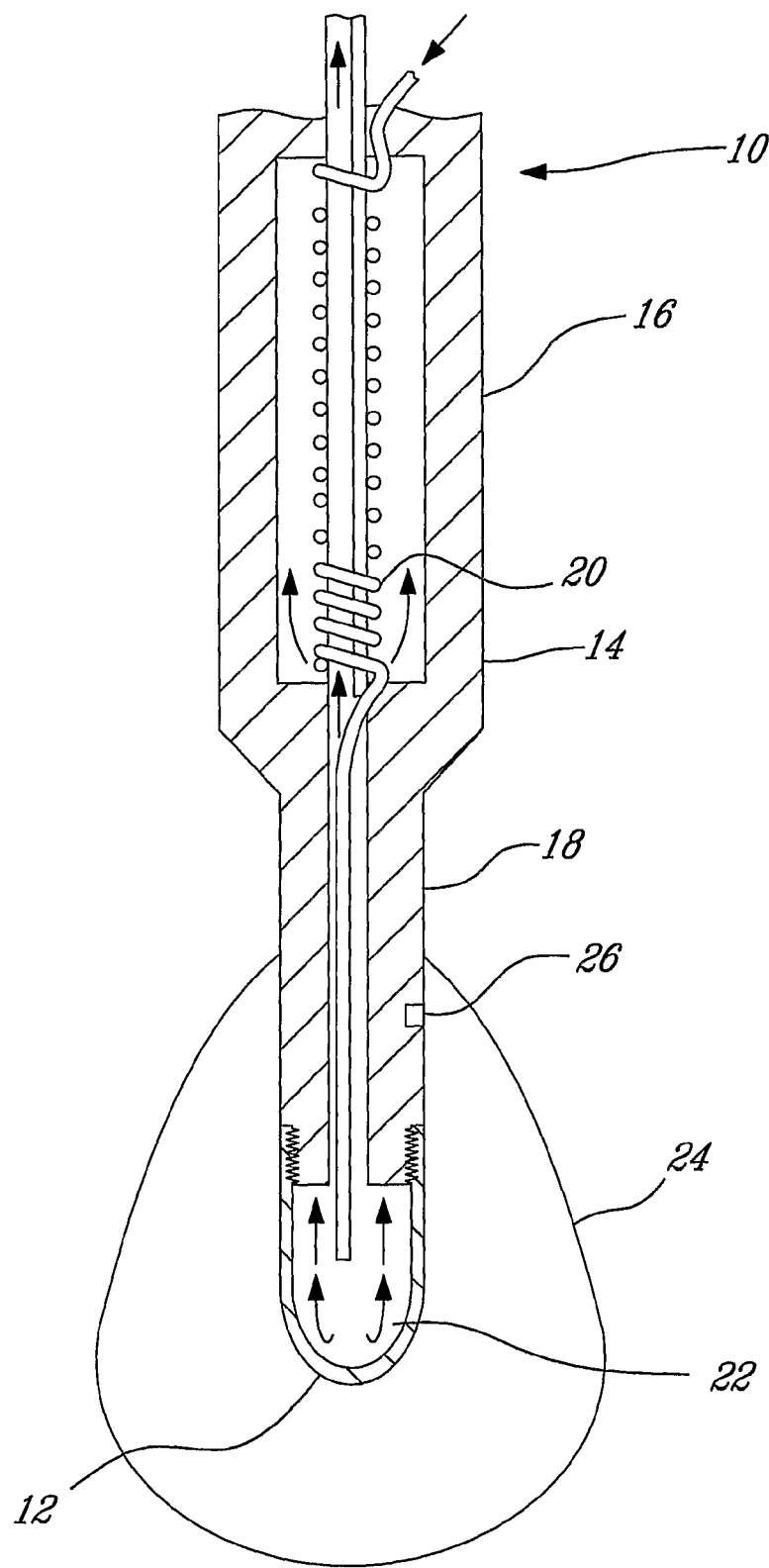
FIG. 1 is a cross-sectional view of a probe according to an embodiment of the invention.

FIG. 1 generally represents a cryoprobe 10. The cryoprobe 10 is fitted with a conductive portion 12, a body 14 that comprises a grabbing portion 16 for holding by a surgeon, and an insulating portion 18. The cryoprobe 10 is typically equipped with a Joule-Thomson cooler 20 for providing a high-pressure gas to a cooling chamber 22 inside the conductive portion 12. When a high-pressure cooling gas such as argon expands in cooling chamber 22, so as to form a cryogenic pool, it effectively cools the surface of conductive portion 12. The conductive portion 12 is made of a thermally conductive material such as stainless steel. The function of the conductive portion 12 is to induce a zone of thermo-surgical temperature in surrounding tissues of a patient. In the case of cryotherapy, this zone of thermo-surgical temperature corresponds to a treated tissue zone having the shape of an ice ball of treated tissues 24, created around the conductive portion 12. Thermo surgical temperatures are temperatures that induce irreversible damages to treated tissues.

Alternatively, a high-pressure heating gas such as helium may be used for operating conductive portion 12 in a heating mode via a reverse Joule-Thomson process, so as to enable treatment by cycles of cooling-heating, and further for shortening the treatment time by thawing the ice ball of treated tissues 24 and preventing it to stick to the cryoprobe 10 when extracting the cryoprobe 10 from the patient's body.

The insulating portion 18 of the body 14 is made of an insulating material such as Teflon. Alternatively, the whole body 14 could be made of the insulating material. This allows for preventing surrounding tissues that need not be desensitized by cryotherapy from being affected by the cold. The insulating portion 18 is fitted with a temperature sensor 26. The temperature sensor 26 senses the temperature of surrounding tissues and in use, the temperature of the ice ball of treated tissues 24.

Figure 2:
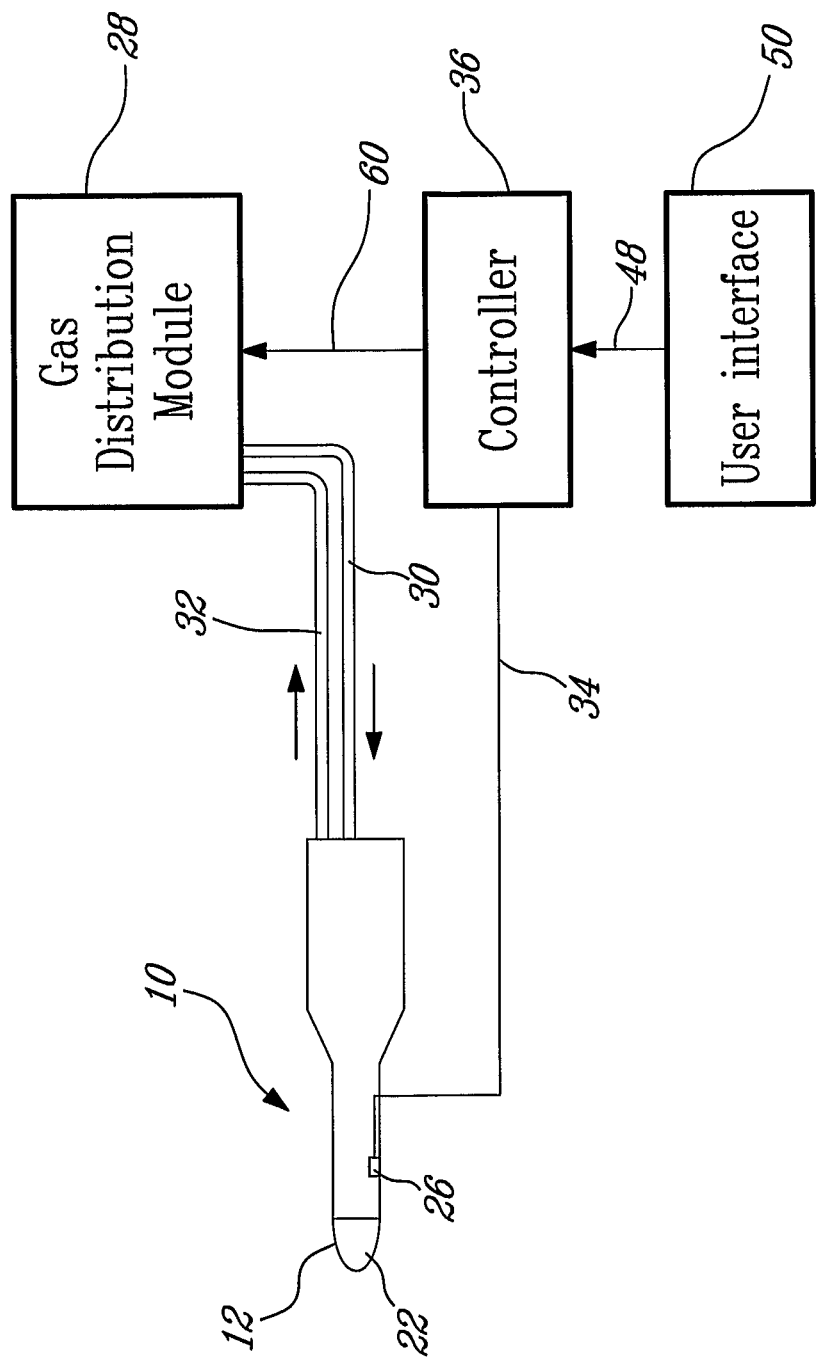
FIG. 2 is schematic view of a system for percutaneous thermotherapy according to another embodiment of the invention.

Turning now to FIG. 2, a gas distribution module 28 controls the flow of pressurized gas, such as argon, into the cryoprobe 10 thorough delivery tube 30. The gas, upon expanding into the cooling chamber 22, cools the conductive portion 12. The gas then returns to the gas distribution module 28 through return tube 32. As the conductive portion 12 gets cooled, the tissues surrounding the conductive portion become frozen and the ice ball of treated tissues 24 starts forming around the conductive portion 12. As the process continues, the ice ball grows in size. The temperature sensor 26 records a decrease in body temperature and sends a signal 34 to a controller 36. The controller 36 compares the temperature signal 34 sent by the temperature sensor 26 with a threshold temperature. Although it may be otherwise, the water freezing temperature (0° C.) is often used as the threshold temperature. Hence, the temperature sensor 26 is used to monitor the progression of a forming front of the ice ball of treated tissues 24. In order to correlate the temperature at the temperature sensor 26 with a size of the ice ball of treated tissues 24, the temperature sensor 26 is placed at a predetermined position with respect to the conductive portion 12. It is possible to correlate different temperatures than 0° C. with the size of ice ball of treated tissues 24 by modeling the response of the tissues to temperature changes as a function of time. However, it has been found that monitoring the forming front of the ice ball of treated tissues 24 is more convenient and gives a direct indication of the ice ball size. As the ice ball of treated tissues 24 continues to grow in size, the temperature further decreases at temperature sensor 26 until the signal 34 sent to the controller 36 reaches the threshold temperature. At that point, the controller 36 automatically shuts down the gas distribution module 28, thereby stopping the growth of the ice ball of treated tissues 24. Alternatively, the controller 36 may be set-up such that it shuts down the gas distribution module 28 only after a predetermined amount of time has elapsed after the temperature sensor 26 has read the threshold temperature or only when the temperature sensor 26 has read a predetermined shut down temperature that is different from the threshold temperature. It will be understood that when the controller 36 shuts down the gas distribution module 28 when the temperature sensor 26 reads the threshold temperature, it is because the shut don temperature is set up to be the same as the threshold temperature. Typically, the temperature sensor 26 is located on the insulating portion 18 approximately 10 mm from the conductive portion. A user may adjust the controller such as to vary the size of the ice ball of treated tissues 24. Another way of adjusting the size of the ice ball of treated tissues 24 is to locate the temperature sensor 26 at different longitudinal positions from the conductive portion 12. This may be either accomplished by having different models of cryoprobe 10 where the temperature sensor 26 is located at different distances from the conductive portion 12, or by providing the cryoprobe with many temperature sensors 26 that are located at different longitudinal positions along the insulated portion 24 of the cryoprobe 10. Then, the controller decides which temperature sensor 26 to monitor. This information may also be provided manually to the controller 36 by a user.

For better reliability, it is possible to equip the insulating portion 18 with more than one temperature sensor 26 at the same distance from the conductive portion 12. The controller 36 then processes the information gathered by the temperature sensors 26 and takes a decision to shut down or to continue cooling accordingly.

The details of the structure of the cooling system used in the probe are well known in the art and as such will not be described in further details in the present description.

Figure 3:
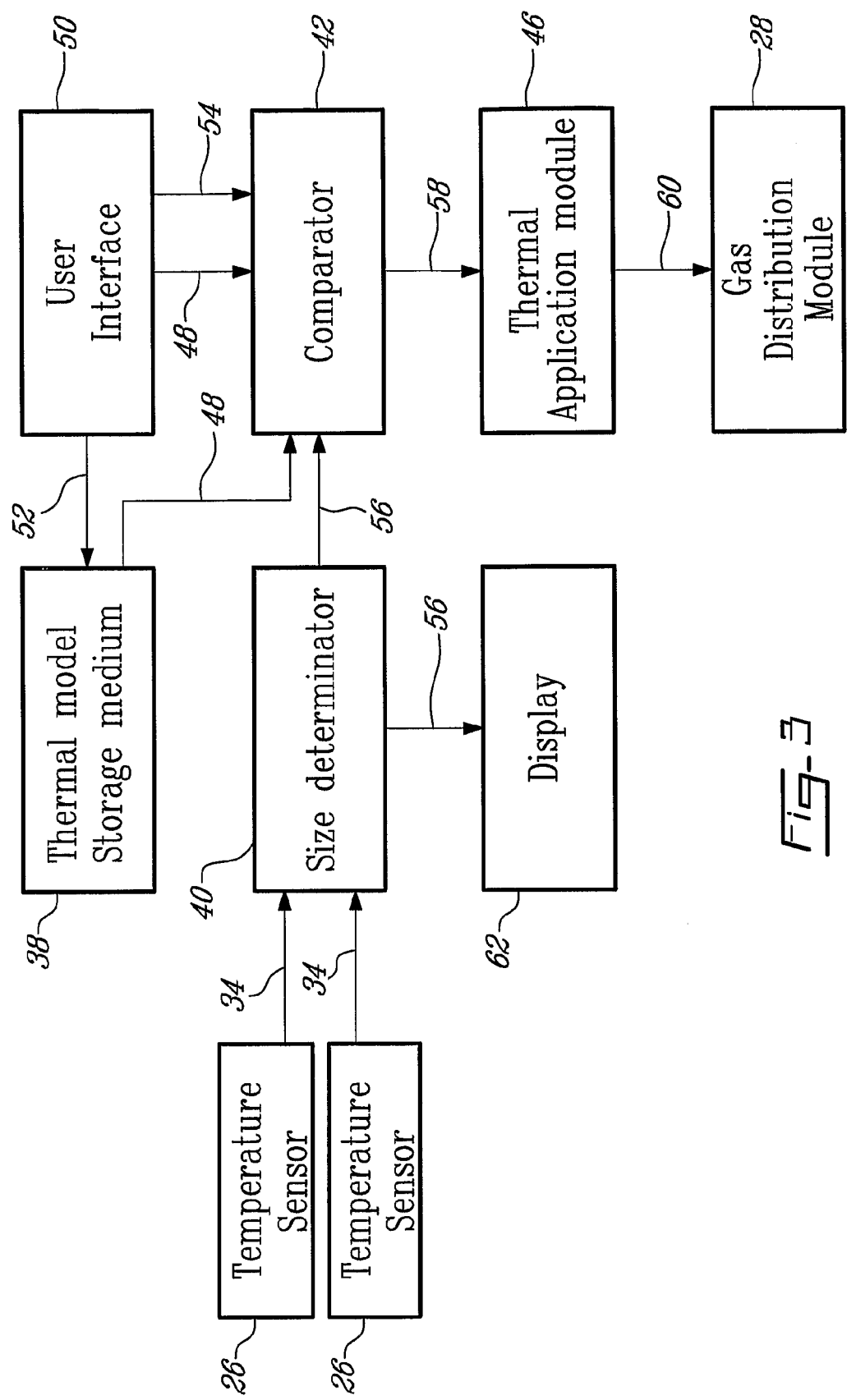
FIG. 3 is a schematic view of a system for percutaneous thermotherapy according to another embodiment of the invention.

FIG. 3 schematically shows the detail of the controller 36, which may be a computer. The controller 36 comprises a thermal model storage medium 38, a size determinator 40, a comparator 42 and a thermal application module 46. The thermal model storage medium 38 stores all thermal models. The thermal models are mathematical models of heat transfer in a body based on parameters such as the type of surgery, type of tissue, type of gas used for cooling, probe model, etc. For instance, tissue types vary whether they are intradiscal or interdiscal tissues, flesh surrounding prostate gland, etc. The thermal model includes the size of the ice ball of treated tissues 24. The thermal model storage medium 38 feeds a desired size signal 48 to the comparator 42. From a user interface 50, the surgeon may select a thermal model desired 52. Optionally, the surgeon may bypass the thermal model storage medium 38 and impose the size of the ice ball of treated tissues 24 with the desired size signal 48 of his own. Optionally, the surgeon may bypass all parameters. The surgeon sends a start command 54, through the user interface 50, to the comparator 42. The size determinator 40 determines the actual size of the ice ball of treated tissues 24 based on the signal 34 received from the temperature sensor or sensors 26. The comparator 42 compares an actual size signal 56 received from the size determinator 40 with desired size signal 48 received from the thermal model 52. Whenever the actual size signal 56 indicates a smaller size than the desired size signal 48, the comparator 42 sends an "ON" signal 58 to the thermal application module 46. In turns, the thermal application module 46 sends a thermal application command signal 60 to the gas distribution module 28 to send cooling gas to the probe 10. Preferably, the size determinator 40 is hooked to a display 62 to show the surgeon the actual size of the ice ball of treated tissues 24.

Figure 4:
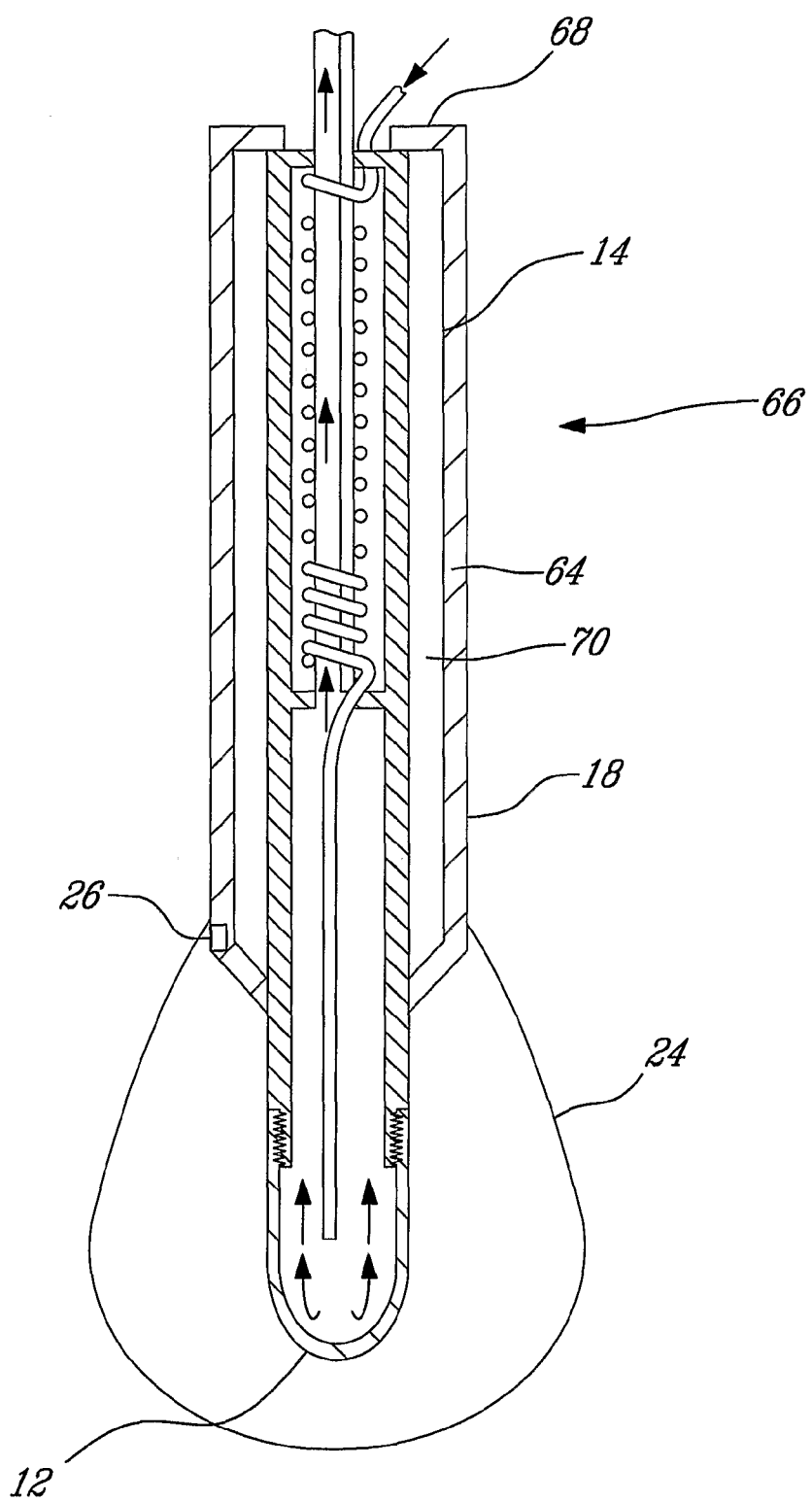
FIG. 4 is a cross-sectional view of a sleeve for a standard probe for use in disc surgery according to an embodiment of the invention.
Figure 5:
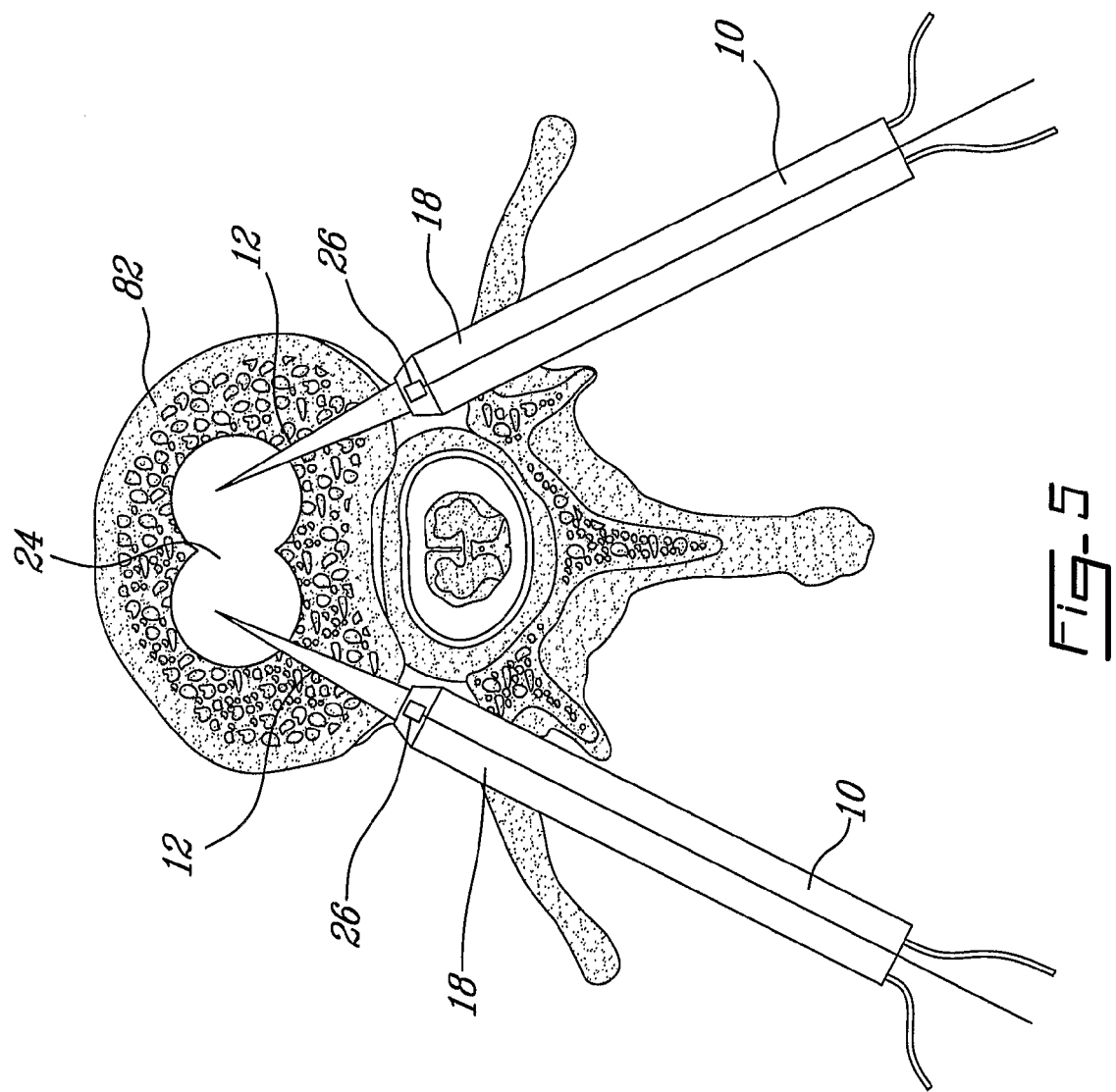
FIG. 5 is a cross-sectional view of a spine where two probes of FIG. 4 are placed for disc surgery.

FIG. 4 shows another embodiment of the invention. In this case, a sleeve 64 having an insulating portion 18 is fitted over a standard cryoprobe 66 which has its body 14 ended by the conductive portion 12. In the present description, the term "sleeve" is used to describe a device that covers a probe and that may be either open at both its extremities, or closed at one extremity. In the present embodiment, the sleeve 64 is open at both extremities. The sleeve 64 is specially designed to fit over a given model of standard cryoprobe 66. The sleeve 64 is equipped with the temperature sensor 26. The sleeve 64 is positioned over the body 14 such that the conductive portion 12 extends from the sleeve 64. Similarly to the previous embodiment, in use, the ice ball of treated tissues 24 forms at the conductive portion 12 and grows until it reaches the temperature sensor 26, which continuously sends a signal to the controller 36 (not shown in the Figure). The position of the temperature sensor 26 on the sleeve 64 is adjusted so that the longitudinal position of the temperature sensor 26 with respect to the conductive portion 12 corresponds to the desired size of ice ball of treated tissues 24. The position of the temperature sensor 26 with respect to the conductive portion 12 may be set by way of locating means 68. Here, the locating means 68 are depicted as a stopper against which the standard cryoprobe 66 abuts. However, the locating means could be a mark on the standard cryoprobe 66 or simply an edge of the sleeve 64 used to locate the sleeve 64, and therefore the temperature sensor 26, with respect to the conductive portion 12. Optionally, the sleeve 64 may comprise an air chamber 70, which also thermally insulates the temperature sensor 26 from the standard cryoprobe 66. For example, the standard cryoprobe 66 may be 4 mm in diameter, the air chamber 70 may be 1 mm thick and the sleeve 64 may be 2 mm thick, including the air chamber 70. Preferably, Teflon is used as the insulating material of the sleeve 64. As shown in FIG. 5, now concurrently referred to, this type of cryoprobe is particularly well adapted for cryosurgery of discs of a spine.

Figure 6:
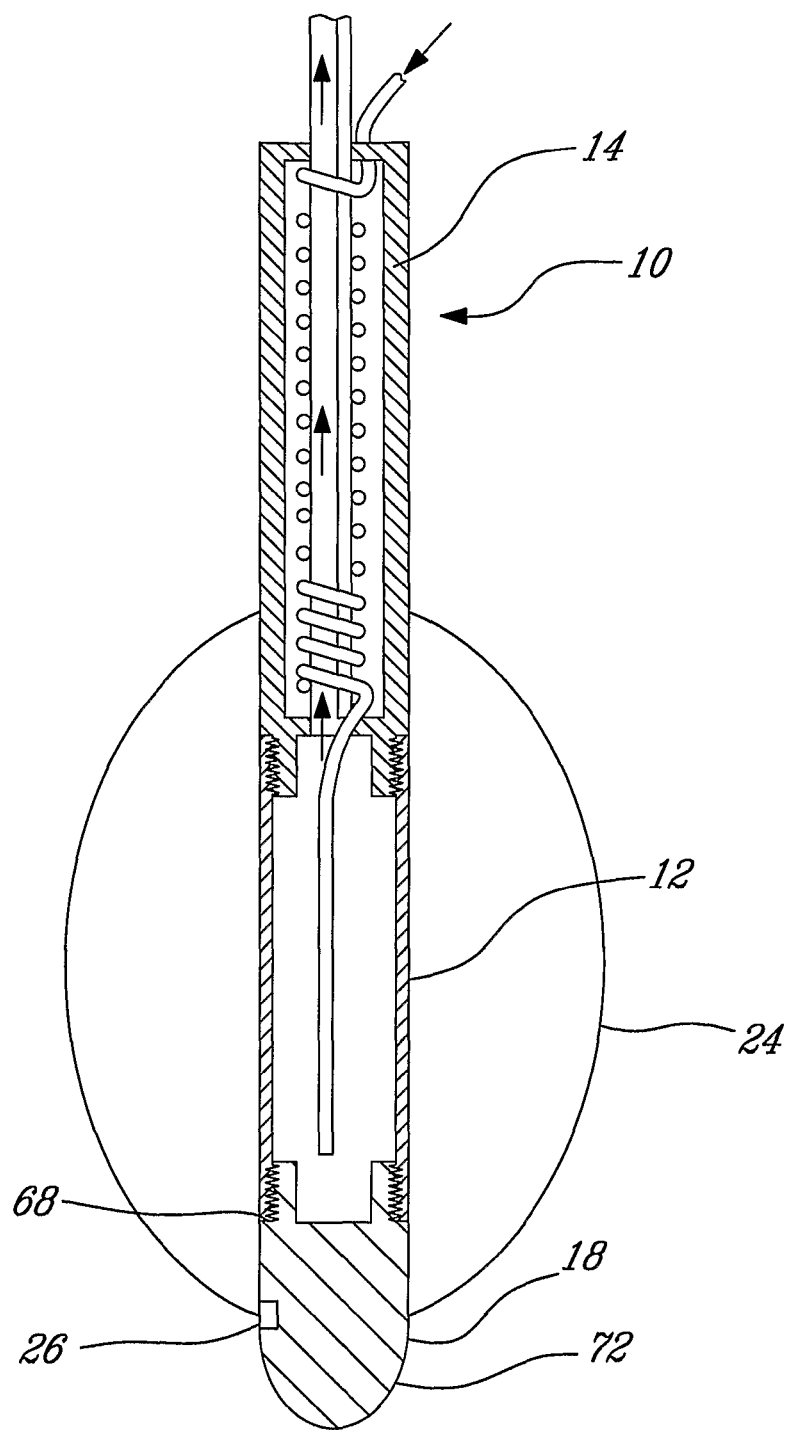
FIG. 6 is a cross-sectional view of a probe for facet surgery according to another embodiment of the invention.
Figure 7:
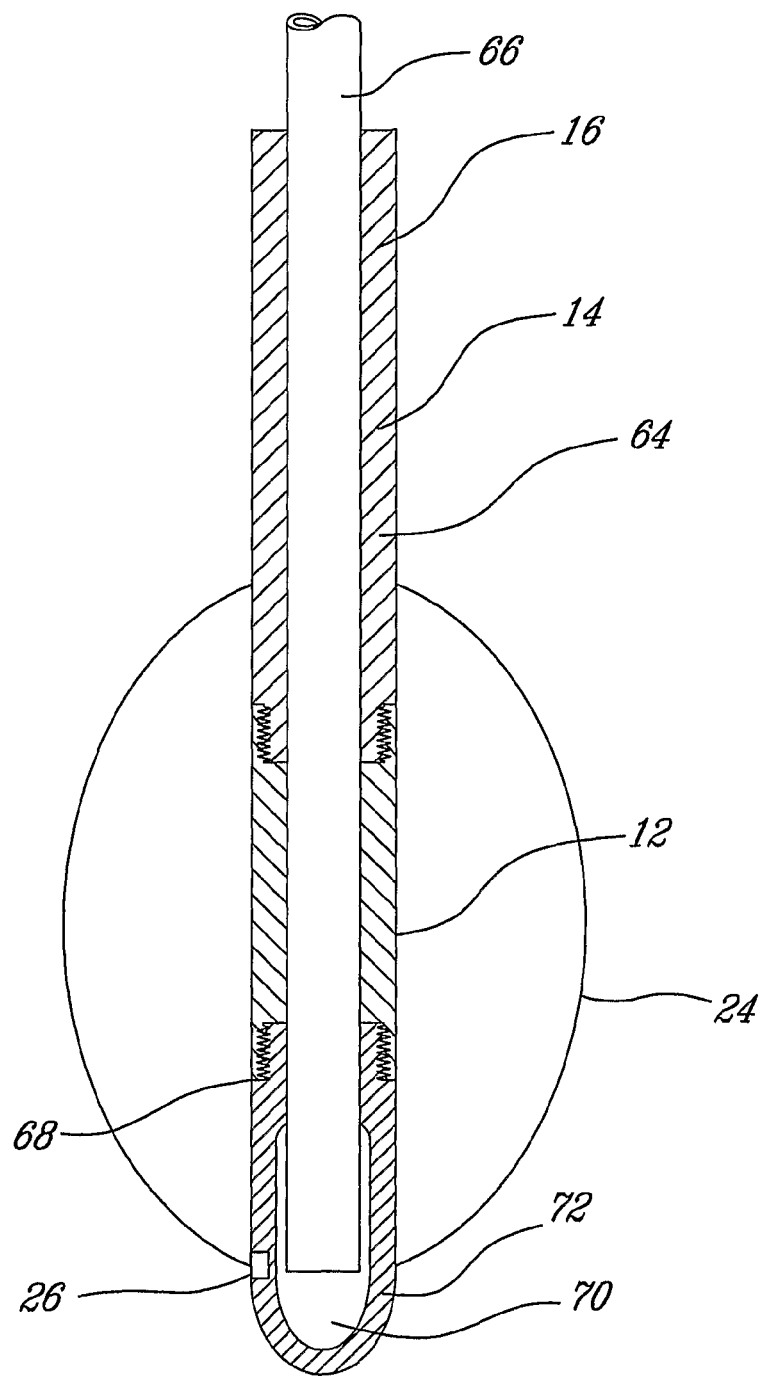
FIG. 7 is a cross-sectional view of a sleeve for a standard probe for use in facet surgery according to another embodiment of the invention.

FIG. 6 shows yet another embodiment of the present invention. This design of cryoprobe 10 is adapted for the cryotherapy of facets, as shown in FIG. 7 and now concurrently referred to. In this embodiment, the conductive portion 12 is not located at a tip 72 of the cryoprobe 10, but rather at a mid-portion of the cryoprobe 10. The tip 72 is made of the insulating material so as to become the insulating portion 18. As can be seen, in the case of facet cryotherapy, the insulating portion 18 is placed at the tip 72 to prevent nerve roots in this spine area from being damaged by the cold. The temperature sensor 26 may be placed on either the insulated tip 72 or the body 14 as long as it is on a thermally insulated portion of the cryoprobe 10 and as long as it is at the predetermined distance from the conductive portion 12 such as to detect a condition of the surrounding tissues. However, it might be advantageous to place the temperature sensor 26 on the insulated tip 72 such as to monitor the ice ball growth closer to the freeze sensitive region where major nerve roots are located. The insulating portion 18 may also be used to position the cryoprobe 10. When the insulating portion 18 abuts a bone or a disc, for example, the conductive portion 12 is in contact with surrounding tissues, such as sensitive nerve cells, where cellular destruction is desired. Positioning the temperature sensor 26 at the insulated tip 72 of the insulating portion 18 enables constant thermal monitoring of the surrounding tissues. Once the temperature sensor 26 detects the front of the ice ball of treated tissues 24, that is when the temperature sensor 26 reads temperatures close to the freezing point, cryotherapy may be automatically stopped if the threshold temperature corresponds with the shut down temperature.

Figure 8:
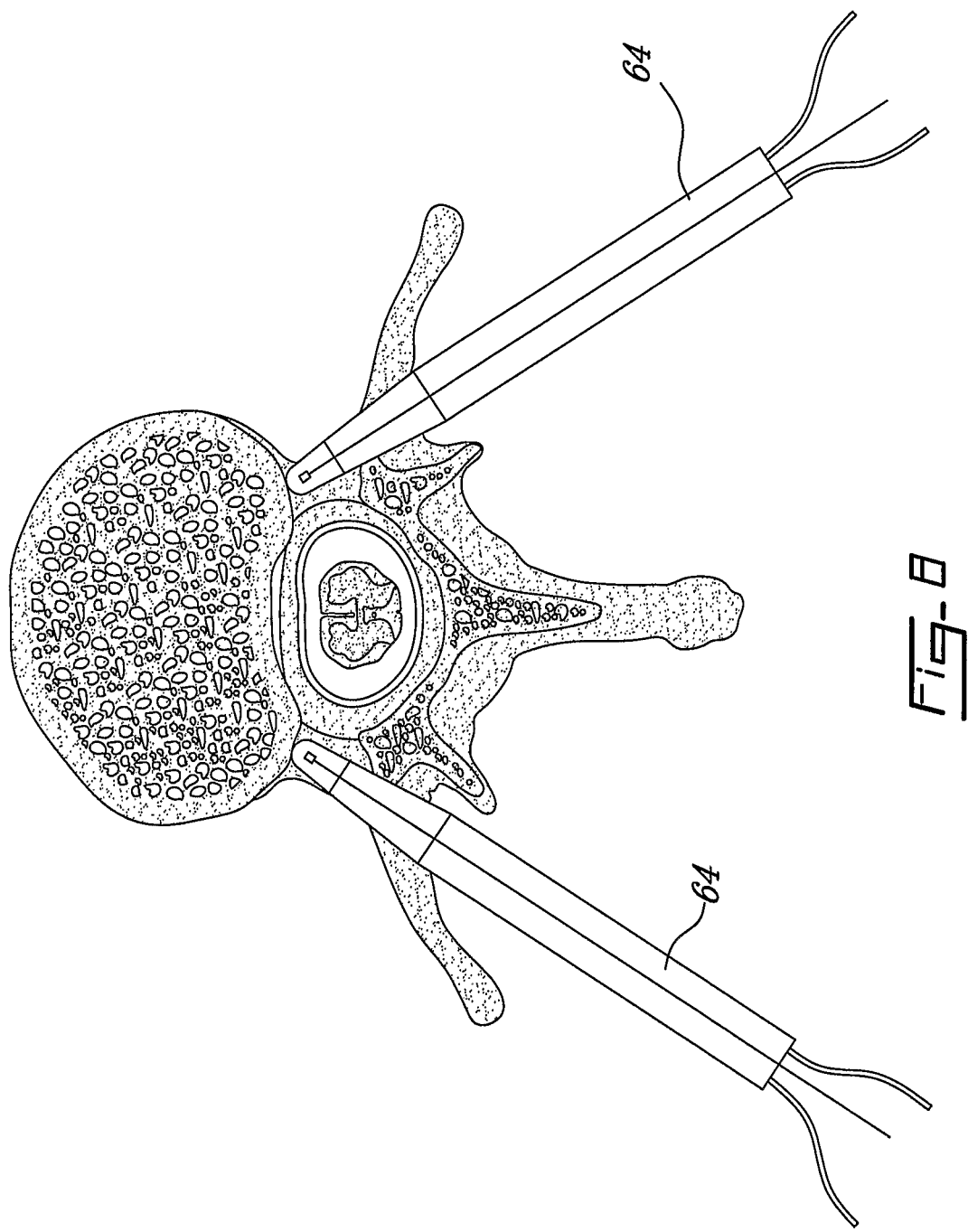
FIG. 8 is a cross-sectional view of a spine where two probes of FIG. 7 are placed for facet surgery.

FIG. 7 depicts a variant of the present embodiment where a sleeve 64, closed at its distal extremity, is fitted to a standard cryoprobe 66. The sleeve 64 comprises the insulated tip 72, the conductive portion 12 and the grabbing portion 16. Optionally, the grabbing portion 16 may be made of metal. However, in this case, gap is required between the standard cryoprobe 66 and the sleeve 64 in the grabbing portion 16. As shown in FIG. 8, now concurrently referred to, this type of cryoprobe is particularly well adapted for cryosurgery of facets joints.

In a particular example, the insulated tip 72 may be 6 mm in diameter and made of an insulating material such as Teflon. An interior air chamber 70 may be provided for added insulation. The temperature sensor 26 is positioned on the insulated tip 72, approximately 6 mm or more from the distal end of the insulated tip 72. The conductive portion 12 is made of a conductive metal and is in contact with the standard cryoprobe 66 inside the sleeve 64. The conductive portion 12 is also 6 mm in outside diameter. The length of the conductive portion 12 depends on the size of the desired treated tissue zone. The standard cryoprobe 66 may be 2 mm in diameter, and the insulated tip 72 may be 1 mm thick, which leaves 1 mm thickness for the air chamber 70.

Figure 9:
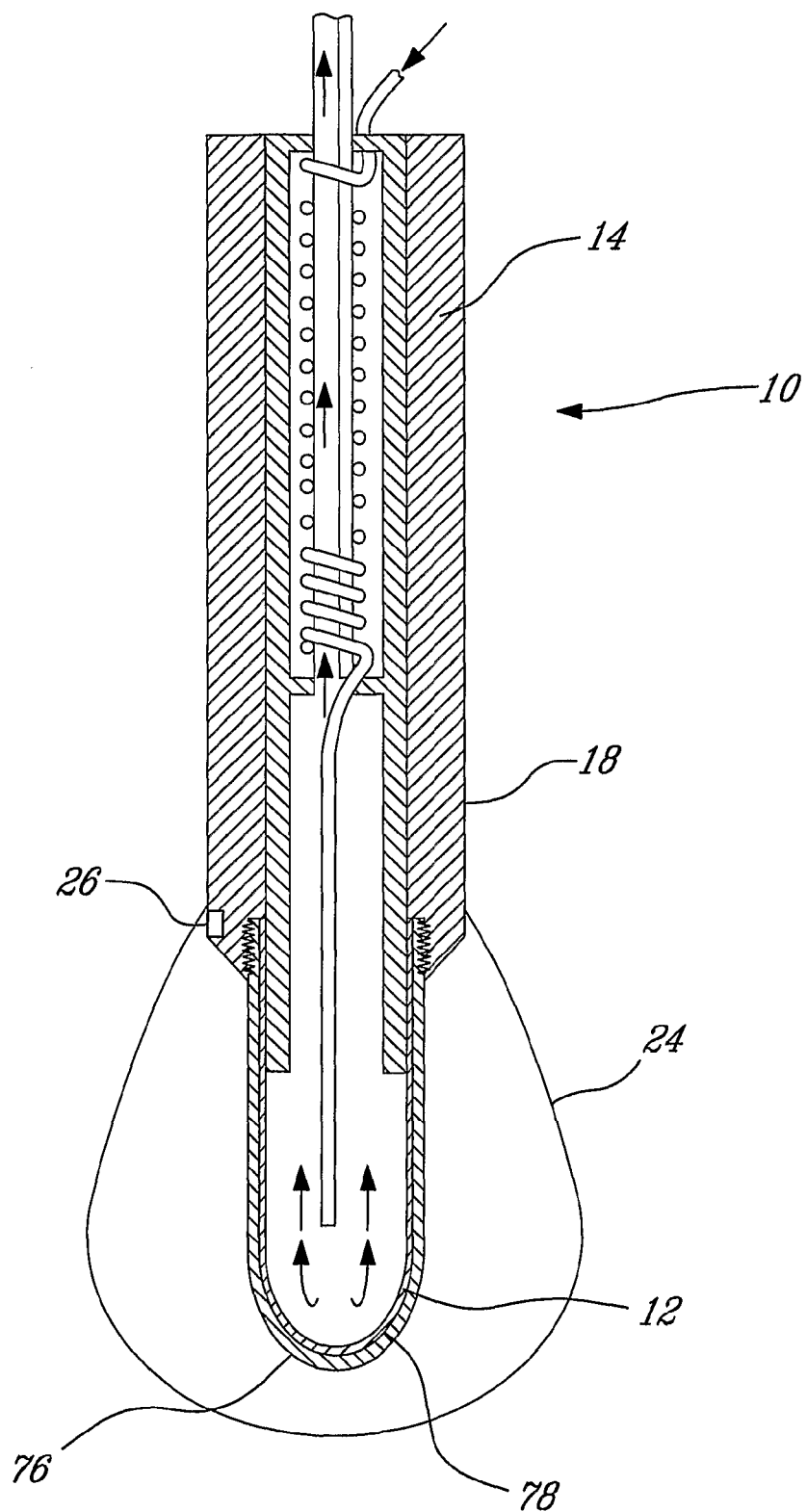
FIG. 9 is a cross-sectional view of a probe according to another embodiment of the invention.

FIG. 9 shows yet another embodiment of the present invention. A thermally conductive tip cover 76 is screwed to the insulating portion 18. The tip cover 76 closely matches the external surface of a probe tip 78 such that heat transfer occurs between the probe tip 78 and the tip cover 76. The temperature sensor 26 is precisely positioned with respect to the probe tip 78 due to the fact that the probe tip 78 bottoms out in the tip cover 76.

Figure 10A:
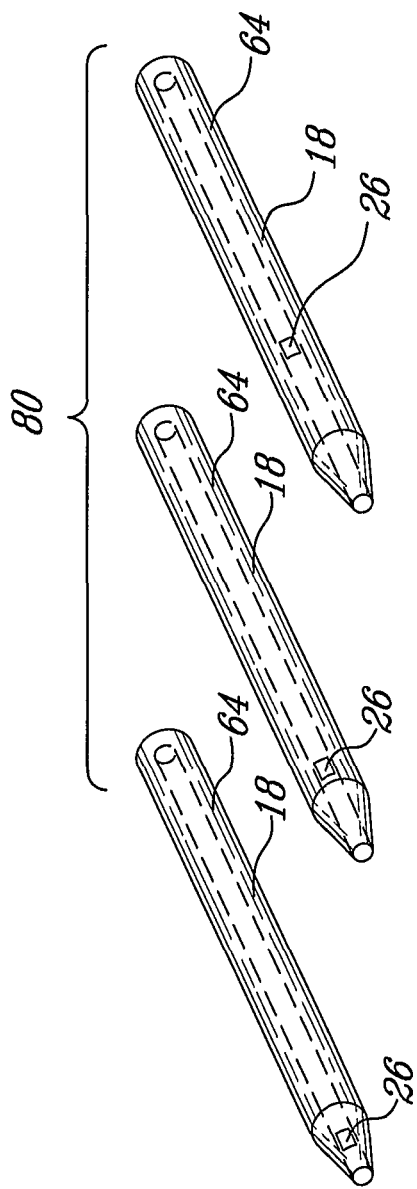
FIG. 10a is a perspective view of a kit of sleeves for standard probes for use in disc surgery according to an embodiment of the invention
Figure 10B:
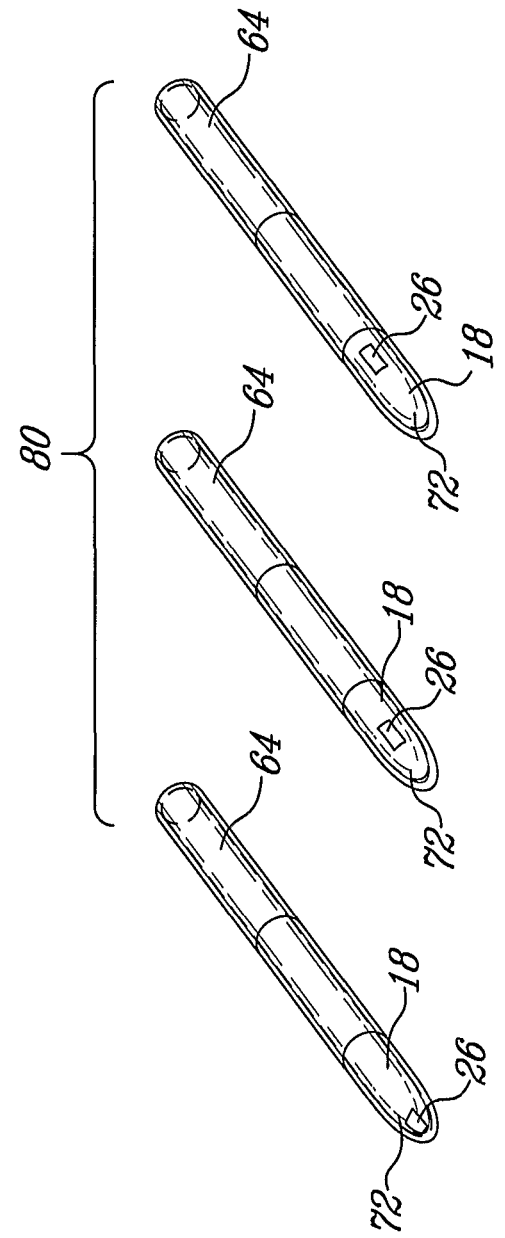
FIG. 10b is a perspective view of a kit of sleeves for a standard probes for use in facet surgery according to another embodiment of the invention.

Now turning to FIGS. 10a and 10b, there is depicted yet another embodiment of the present invention where kits 80 are provided that comprise a plurality of sleeves 64 for fitting to a standard cryoprobe. In FIG. 10a, the kit comprises sleeves 64 having the insulating portions 24. The sleeves 64 are provided with two opposed openings so that the standard cryoprobe protrudes through each sleeve 64, such as described previously and shown in FIG. 4. The only difference between each sleeve 64 of the kit is that the temperature sensor 26 is placed at different longitudinal locations on the insulating portion 18. Hence, a surgeon may select, prior to cryotherapy, the required sleeve 64 depending on the particular needs of the surgery, or depending on the patient. Similarly, in FIG. 10*b*, the kit 80 also comprises sleeves 64. This time, the sleeves 64 are of a close-ended model where the insulating portion 18 corresponds to the insulating tip 72. The sleeves 64 are adapted to fit a standard cryoprobe 66 (not shown in this Figure), such as described previously and shown in FIG. 7. The insulated tips 74 are differentiated from each other by the fact that the temperature sensors 26 are placed at different longitudinal locations from the conductive portion 12, for the particular needs of a given cryosurgery. For convenience, the kit 80, or the sleeves 64 themselves may carry an identification of an ice ball size for each sleeve 64. The ice ball size may be a function of a predetermined body part tissue as the ice ball may grow differently depending on the body part tissue.

Surgery

When operating, the surgeon has to precisely monitor both the placement of the cryoprobe 10 into the patient's body and the growth of the ice ball of treated tissues 24 such as to avoid damaging fragile tissues. With the cryoprobes of prior art, MRI was often used as an imaging system. Advantageously, with the present invention, such costly techniques are not absolutely required since the controller 36 automatically shuts down the gas distribution module 28, thereby not requiring continuous visual monitoring of the growth of the ice ball of treated tissues 24 by the surgeon. With the thermotherapy system of the present invention, less costly and more readily available imaging techniques such as fluoroscopy, diagnostic ultrasound, etc, can be used. Moreover, when using techniques other than MRI, the composition of the cryoprobe 10 is not restricted to non-ferromagnetic materials, which lowers its cost.

Facet Cryosurgery

Reference is now made to FIG. 8. For facet cryosurgery, the cryoprobe 10 is inserted under local anaesthesia using a preliminary trocar through a 6 mm incision. For facet cryotherapy, the cryoprobe 10 is positioned on a posterior-inferior portion of foramina close to the nerve root for protection and the conductive portion 12 is placed alongside a lateral facet joint for joint denervation. Position is verified on both antero-posterior and lateral fluoroscopy.

The freezing process is then started: A first step of freezing takes place at −180° C. (temperatures colder than −140° C. are preferred) while monitoring the growth of the ice ball of treated tissues 24 with the temperature sensors 26. The controller 36 shuts down the gas distribution module 28 when the first temperature threshold is reached, which normally takes approximately 7 minutes. The controller 36 maintains the gas distribution module 28 shut down for 2 minutes for passive thawing to occur. The controller 36 then turns on the gas distribution module 28 once again for a second step of freezing at −180° C. until a second temperature threshold is reached, which takes approximately another 7 minutes. The first and second threshold temperatures may be the same or different, depending on the desired results. To remove the cryoprobes 10, heating the cryoprobes 10 for a few seconds is sometimes required. Stitches are then applied to the patient. The patient is encouraged to resume his normal activities rapidly and weak to moderate analgesia is necessary for the first week. Cryoprobe tract pain normally disappears after one to two weeks.

Discs Cryosurgery

Reference is now made to FIG. 5. For discs cryosurgery, 6 mm pointed trocars are inserted through a 6 mm skin puncture. The trocar is inserted bilaterally to postero-lateral corners of the targeted disc 82 at a 45 degrees angle from the skin at 10 cm from a midline under local anaesthesia with AP and lateral fluoroscopy. Through this trocar is inserted a 2 mm drill to perforate the annulus. The drill is then replaced by the cryoprobe 10 which conductive portion 12 penetrates 1-1.5 cm deep into the disc 82. The insertion into the disc 82 is bottomed by a conic end of the insulating portion 18. Typically, two cryoprobes 10 are used for disc cryosurgery, one on each side of the disc 82. Both cryoprobes 10 should nearly meet in the middle of the disc 82. The freezing process, similar to the one used for facets cryosurgery, is then started while monitoring treated tissues temperatures with the temperature sensors 26 is performed. To remove the cryoprobes 10 and the trocar, heating the cryoprobes 10 for a few seconds is sometimes required. A stitch is then applied to the skin once the cryoprobes 10 are removed and normal activities may be resumed shortly. Mild to moderate analgesia is prescribed for the first week.

While the invention has been described with particular reference to the illustrated embodiment, it will be understood that numerous modifications thereto will appear to those skilled in the art. For example, the assembly of some parts of the probe were depicted as a threaded assembly. However, the person skilled in the art would readily understand that this assembly could also be a snap-fit or other adequate assembly method, for example. Accordingly, the above description and accompanying drawings should be taken as illustrative of the invention and not in a limiting sense.

The invention claimed is:

1. A cryosurgical probe operative to cool target nerve tissue to a temperature below about −140° C. to reduce or eliminate nerve tissue by growing an ice ball, the probe comprising:
   a thermally conductive body having a conductive portion adapted to contact said tissue and form an ice ball thereat by cooling during use;
   a thermally insulating body adjacent to said conductive portion onto which said ice ball forms during use;
   a temperature sensor shut-down switch positioned on said thermally insulating body at a predetermined longitudinal position so that when said thermally insulating body is installed on the thermally conductive body, said temperature sensor shut down switch is at a predetermined longitudinal position with respect to the conductive portion of the thermally conductive body;
   wherein said cooling of said thermally conductive body is shut down when said temperature sensor shut down switch is in contact with said ice ball,
   wherein said ice ball has a predetermined size determined by said temperature sensor shut-down switch predetermined position.

2. The probe of claim 1 wherein said predetermined position corresponds to said temperature sensor shut-down switch reading a temperature equal to or below 0° C. when said predetermined size of the ice ball is reached.

3. The probe of claim 1 wherein said thermally insulating body is a removable sleeve.

4. The probe of claim 1 wherein said conductive body is exposed at a distal tip of said probe.

5. The probe of claim 1 wherein said insulating body is located at a distal tip of said probe and said conductive body is exposed proximal to said tip.

6. A method of manufacturing a cryosurgical probe as defined in claim 1, the method comprising:
determining said predetermined position of said sensor shut down switch as a function of a desired ice ball size and thermal characteristics of the surrounding tissue.

7. The method of claim 6 further comprising the step of positioning said sensor shut down switch on said insulating body of the probe at said predetermined position from said conductive body.

8. A method for performing percutaneous cryotherapy which comprises the use of the probe of claim 1 so as to create said ice ball by cooling said conductive portion, and
shutting down cooling of said conductive portion when said ice ball reaches said temperature sensor shut-down switch on said insulating body.

9. The method of claim 8 further comprising initially positioning said probe using imaging and cooling said conductive portion without a live imaging.

10. The method of claim 9 wherein said step of cooling comprises cooling at least partially said surrounding tissues to a temperature below −140° C.

11. The method of claim 10 wherein said temperature is approximately −180° C.

12. The method of claim 10 wherein said step of stopping occurs when said temperature sensor shut-down switch has detected a temperature of approximately 0° C.

13. The method of claim 12 further comprising cooling a second time said conductive portion so as to create said ice ball of said surrounding tissues, said step of cooling a second time comprising at least partially cooling said surrounding tissues to a temperature of approximately −180° C.

14. The method of claim 8 using two probes.

15. The method of claim 8 for treating lumbar discs pain.

16. The method of claim 8 for treating spinal facet joint syndrome.

17. A sleeve for fitting over a cryosurgical probe having a conductive portion, said cryosurgical probe being operative to cool target nerve tissue to a temperature below about −140° C. to reduce or eliminate nerve tissue by growing an ice ball having a predetermined size, the sleeve comprising:
a thermally insulating body;
a locating means on said thermally insulating body, and
a temperature sensor shut-down switch positioned on said thermally insulating body at a predetermined longitudinal distance from said locating means so that when said sleeve is installed on the cryosurgical probe, said temperature sensor shut-down switch is at a predetermined longitudinal position with respect to the conductive portion of the cryosurgical probe.

18. The sleeve of claim 17 wherein said insulating body has both extremities open for accommodating the cryosurgical probe through said insulating body.

19. The sleeve of claim 18 wherein said insulating body is locally recessed for providing a local air gap between said insulating body and the cryosurgical probe.

20. The sleeve of claim 18 wherein said sleeve is removable from the cryosurgical probe.

21. The sleeve of claim 18 wherein said insulating body is equipped with a plurality of said temperature sensor shut-down switch.

22. The sleeve of claim 17 further comprising a thermally conductive body adjacent said insulating body, said conductive body being adapted to contact the conductive portion of the cryosurgical probe and transmit heat from the surrounding tissue to the conductive portion, said conductive body being operative to form the ice ball thereat during use.

23. The sleeve of claim 22 wherein said sleeve has a closed ended tip, said conducting body being located at said tip.

24. The sleeve of claim 22 wherein said sleeve has a closed ended tip, said insulating body being located at said tip.

25. A method of manufacturing a sleeve as defined in claim 17, the method comprising:
determining said predetermined position of said sensor shut down switch as a function of a desired ice ball size and thermal characteristics of said surrounding tissue.

26. The method of claim 25 further comprising the step of positioning said temperature sensor shut-down switch on said insulating body at said predetermined position.

27. A system for percutaneous thermotherapy comprising:
a controller; and
a probe as defined in claim 1, said temperature sensor shut-down switch being operative to send a temperature signal to said controller,
wherein said controller is operative to control said cooling of said conductive portion based on said temperature signal sent by said temperature sensor shut-down switch.

28. The system of claim 27 wherein said controller stops said cooling of said conductive portion when said temperature signal has reached a threshold value.

29. The system of claim 28 wherein said controller is adjustable to control the size of the ice ball.

30. The system of claim 29 wherein said controller further controls the size of the ice ball based on time.

31. The system of claim 30 wherein said insulating portion has a plurality of said temperature sensor shut-down switch, each said temperature sensor shut-down switch being operative to send said temperature signal to said controller, said controller comparing the difference between said temperature signals received with a discrepancy threshold, said controller being operative to shut down said cooling of said conductive portion if said difference is above said discrepancy threshold.

32. A kit comprising at least two sleeves as defined in claim 17, each one of the at least two sleeves having its said temperature sensor shut-down switch located at a different longitudinally position.

33. The kit of claim 32 further comprising a controller responsive to a signal received from said temperature sensor shut-down switch, said controller being operative to control a cooling of the conductive portion of the cryosurgical probe.

34. The kit of claim 32 further comprising an identification of an ice ball size corresponding to each of said probes for a predetermined body tissue.

35. The sleeve of claim 17, wherein said temperature sensor shut-down switch is proximate an extremity of said insulating body so that when said sleeve is installed on the cryosurgical probe, said extremity is proximate the conductive portion of the cryosurgical probe.

36. A kit comprising at least two cryosurgical probes as defined in claim 1, each one of the at least two probes having its temperature sensor shut-down switch located at a different longitudinally distance from said conductive portion.

37. The kit of claim 36 further comprising a controller responsive to a signal received from said temperature sensor shut-down switch, said controller being operative to control a cooling of said conductive portion.

38. The kit of claim 36 further comprising an identification of an ice ball size corresponding to each of said probes for a predetermined body tissue.

39. A method for performing percutaneous cryotherapy comprising the step of automatically shutting down by a temperature sensor shut-down switch an imposed thermal variation of a conductive portion of a cryoprobe inserted in a patient's body once a signal from a single temperature sensor shut-down switch placed on a thermally insulating portion of said cryoprobe for sensing a size of an ice ball in surrounding tissues has reached a predetermined size.

* * * * *